(12) United States Patent
Lee (10) Patent No.: US 8,182,760 B2
(45) Date of Patent: May 22, 2012

(54) STEAM STERILIZER

(76) Inventor: Wen Ching Lee, Taichung (TW)

( * ) Notice: Subject to any disclaimer, the term of this patent is extended or adjusted under 35 U.S.C. 154(b) by 90 days.

(21) Appl. No.: 12/919,334

(22) PCT Filed: Dec. 23, 2009

(86) PCT No.: PCT/CN2009/075887
§ 371 (c)(1),
(2), (4) Date: Aug. 25, 2010

(87) PCT Pub. No.: WO2010/072151
PCT Pub. Date: Jul. 1, 2010

(65) Prior Publication Data
US 2011/0020193 A1 Jan. 27, 2011

(30) Foreign Application Priority Data
Dec. 25, 2008 (CN) ...................... 2008 2 0179010 U (51) Int. Cl.
*A61L 2/07* (2006.01)
(52) U.S. Cl. .......... 422/298; 422/26; 422/300; 126/344; 126/348
(58) Field of Classification Search .................... 422/26, 422/292, 298, 300; 126/344, 348
See application file for complete search history.

(56) References Cited

U.S. PATENT DOCUMENTS
2010/0193528 A1* 8/2010 Davidson ................... 220/573.1

FOREIGN PATENT DOCUMENTS
| | | | |
|---|---|---|---|
| CN | 2464339 Y | 12/2001 |
| CN | 2586426 Y | 11/2003 |
| CN | 2710638 Y | 7/2005 |
| CN | 2836806 Y | 11/2006 |
| CN | 201324391 Y | 10/2009 |
| KR | 100557821 B | 3/2006 |

* cited by examiner

*Primary Examiner* — Sean E Conley
(74) *Attorney, Agent, or Firm* — Rosenberg, Klein & Lee (57) ABSTRACT

The present invention provides a steam sterilizer including a primary container and a secondary container. The primary container includes a primary base. The interior of the primary base is provided with a heating means. The surface of the primary base is covered by a primary box having a downward opening. The secondary container movably covers the top of the primary box. The secondary container includes a secondary base. The surface of the secondary base is covered by a secondary box having a downward opening. The top of the primary box is provided with a primary through-hole for allowing steam to flow through. The bottom of the secondary base is provided with a secondary through-hole corresponding to the primary through-hole. The secondary container is movably disposed on the top of the primary container to share the steam.

8 Claims, 9 Drawing Sheets

STEAM STERILIZER

BACKGROUND OF THE INVENTION

1. Field of the Invention

The present invention relates to a steam sterilizer, and in particular to a multi-function and composite steam sterilizer.

2. Description of Prior Art

Since infants have a low resistance, more attention has to be paid in order to protect the infant against the invasion or infection of bacteria. Thus, feeding bottles, feeding nipples, pacifiers, eating utensils and even toys for the infant have to be often sterilized. The above-mentioned sterilization may be carried out by different ways such as high-temperature steam or ultra-violet beams. The high-temperature steam is often used to change the protein structure of bacteria and to suppress the propagation of bacteria. Currently, the high-temperature steam for sterilization is generated by boiling water, so that a bottle sterilizer for sterilizing feeding bottles is also called a steam sterilizer by the manufacturers in this field.

The existing steam sterilizer includes a primary container. The primary container includes a primary base in which a heating means is provided. The surface of the primary base is provided with a water tray. The surface of the primary base is covered by a primary box having a downward opening.

The water received in the water tray is heated by the heating means. Then, the steam pervades the interior of the primary box for sterilization. However, such a steam sterilizer has problems as follows. The feeding bottle has a certain height and is usually disposed upright in the steam sterilizer. Thus, the steam sterilizer also has a height large enough to receive the upright bottles. When a user intends to put the feeding bottles in a microwave oven for further sterilization, the feeding bottles have to be taken off from the primary box and then disposed in the microwave oven. Otherwise, the whole steam sterilizer has to be put in the microwave oven. However, the stem sterilizer cannot be put upright into the microwave oven. Further, since the interior of the steam sterilizer is provided with the heating means, the heating means may suffer damage if it is put in the microwave oven. Also, the steam sterilizer is made of materials which cannot sustain the high temperature within the microwave oven. Thus, the existing steam sterilizer is unsuitable to be put into the microwave oven.

SUMMARY OF THE INVENTION

In view of the above-mentioned problems in prior art, the present Inventor proposes a multi-function and composite steam sterilizer.

The present invention provides a steam sterilizer including a primary container and a secondary container. The primary container includes a primary base. The interior of the primary base is provided with a heating means. The surface of the primary base is covered by a primary box having a downward opening. The secondary container movably covers the top of the primary box. The secondary container includes a secondary base. The surface of the secondary base is covered by a secondary box having a downward opening. The top of the primary box is provided with a primary through-hole for allowing steam to flow through. The bottom of the secondary base is provided with a secondary through-hole corresponding to the primary through-hole. The secondary container is movably disposed on the top of the primary container to share the steam. Since the secondary container is movably disposed on the top of the primary box of the primary container, the primary container and the secondary container share the steam for sterilization by means of the primary through-hole and the secondary through-hole in a normal condition. Further, the primary container and the secondary container may be made of suitable materials that can sustain the high temperature within the microwave oven, so that the secondary container can be alone disposed in the microwave oven.

Further, according to the present invention, the bottom of the secondary base is provided with a trough corresponding to the top of the primary box. The periphery of the trough is formed into a stepped portion for enclosing the outer edge of the top of the primary box. The stepped portion is configured to prevent the secondary container from falling off from the primary container.

Further, according to the present invention, the top surface of the primary base is provided with a first tray. The first tray is provided with a plurality of perforations. The first tray may be movably provided on the top surface of the primary base. Thus, if the primary box has a suitable height and the primary box and the first tray are made of materials that can sustain the high temperature within the microwave oven, the primary box and the first tray can be disposed in the microwave oven.

After the primary container, the secondary container and the first tray are disposed in the microwave oven and a sterilizing process is carried out in the microwave oven, a user can use a fourth tray to support the primary container, the secondary container and the first tray, so that the user may not get hurt due to their high temperature.

In comparison to prior art, according to the present invention, since the secondary container is movably disposed on the top of the primary box of the primary container, the primary container and the secondary container share the steam for sterilization by means of the primary through-hole and the secondary through-hole in a normal condition. Further, the primary container and the secondary container may be made of suitable materials that can sustain the high temperature within the microwave oven, so that the secondary container can be alone disposed in the microwave oven.

BRIEF DESCRIPTION OF THE DRAWINGS

FIG. 7 is a perspective view showing that the secondary box covers the primary base and a breast pump is disposed there between;

DETAILED DESCRIPTION OF THE INVENTION

In order to further understand the structure, technical features and embodiments of the present invention, a detailed description relating thereto will be made with reference to the accompanying drawings. The present invention relates to a steam sterilizer including a primary container 1 and a secondary container 2.

Figures 1, 1A:
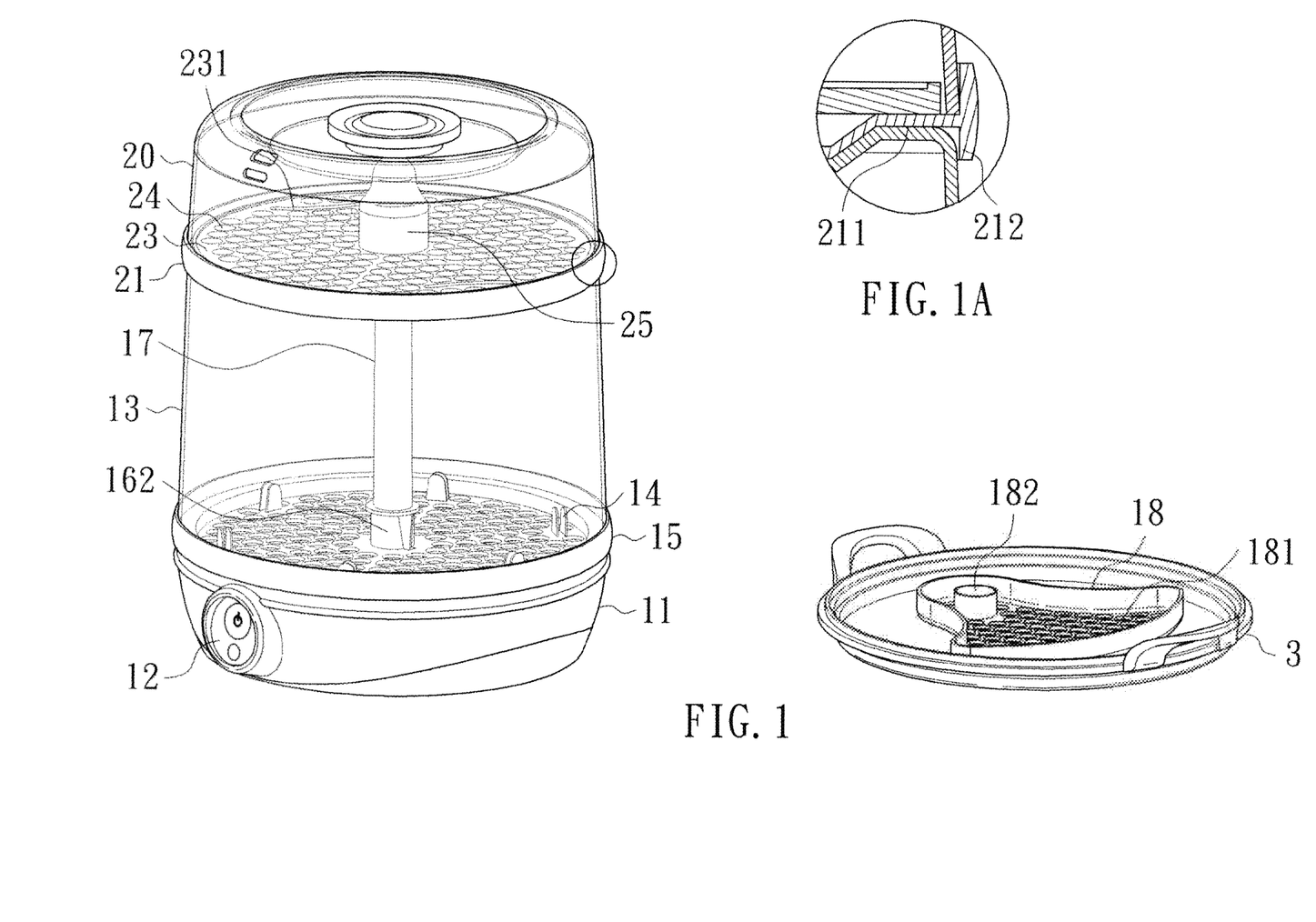
FIG. 1 is a partially enlarged perspective view of the present invention.

The primary container 1 includes a primary base 11. The interior of the primary base 11 is provided with a heating means 121. The surface of the primary base 11 is covered by a primary box 13 having a downward opening. The primary base 11 is provided with a water tray 121 in communication with the primary box 13. The heating means 12 is activated by a switch button 12 for heating the water in the water tray 122 to generate steam. The top of the primary box 13 is provided with a primary through-hole 131 for allowing the steam to flow through. The top surface of the primary base 11 is provided with a first tray 15. The first tray 15 is provided with a plurality of perforations 151. The first tray 15 is provided with two spaced primary clip wings 162. An insertion hole 161 is formed between the two primary clip wings 162. The insertion hole 161 allows a pipe 17 to be inserted thereto firmly because the primary clip wings 162 are made of elastic materials. The first tray 15 is further provided with at least one pair of spaced secondary clip wings 14. The mouth of a feeding bottle can be inserted into the gap formed between the secondary clip wings 14 because the secondary clip wings 14 are made of elastic materials. An upper section of the pipe 17 is inserted into the primary through-hole 131. The pipe 17 may be disposed through a second tray 18 as shown in FIG. 1. The second tray 18 is provided with a plurality of perforations 181. The second tray 18 is provided with a channel 182 for allowing the pipe 17 to be disposed through. The second tray 18 may be optionally removed from the primary container 1 as shown in FIG. 1.

The secondary container 2 is movably provided on the top of the primary box 13. The secondary container 2 includes a secondary base 21. The surface of the secondary base 21 is covered by a secondary box 20 having a downward opening. The height of the secondary box 20 is slightly smaller than that of the primary box 13. The bottom of the secondary base 21 is provided with a secondary through-hole 22 corresponding to the primary through-hole 131. The secondary through-hole 22 allows the top of the pipe 17 to be disposed through, so that the secondary container 2 can be movably disposed on the top of the primary container 1 to share the steam. The bottom of the secondary base 21 is provided with a trough 211 corresponding to the top of the primary box 13. The periphery of the trough 211 is formed into a stepped portion 212. The stepped portion 212 encloses the outer edge of the top of the primary box 13 for preventing the secondary container 2 from falling off the primary container 1. The top surface of the secondary container 21 is movably provided with a third tray 23. The third tray 23 is provided with a plurality of perforations 24. The surface of the third tray 23 is provided with a post 25 for allowing the mouth of the feeding bottle to be put thereon.

The steam sterilizer of the present invention can be used in different ways.

Figure 2:
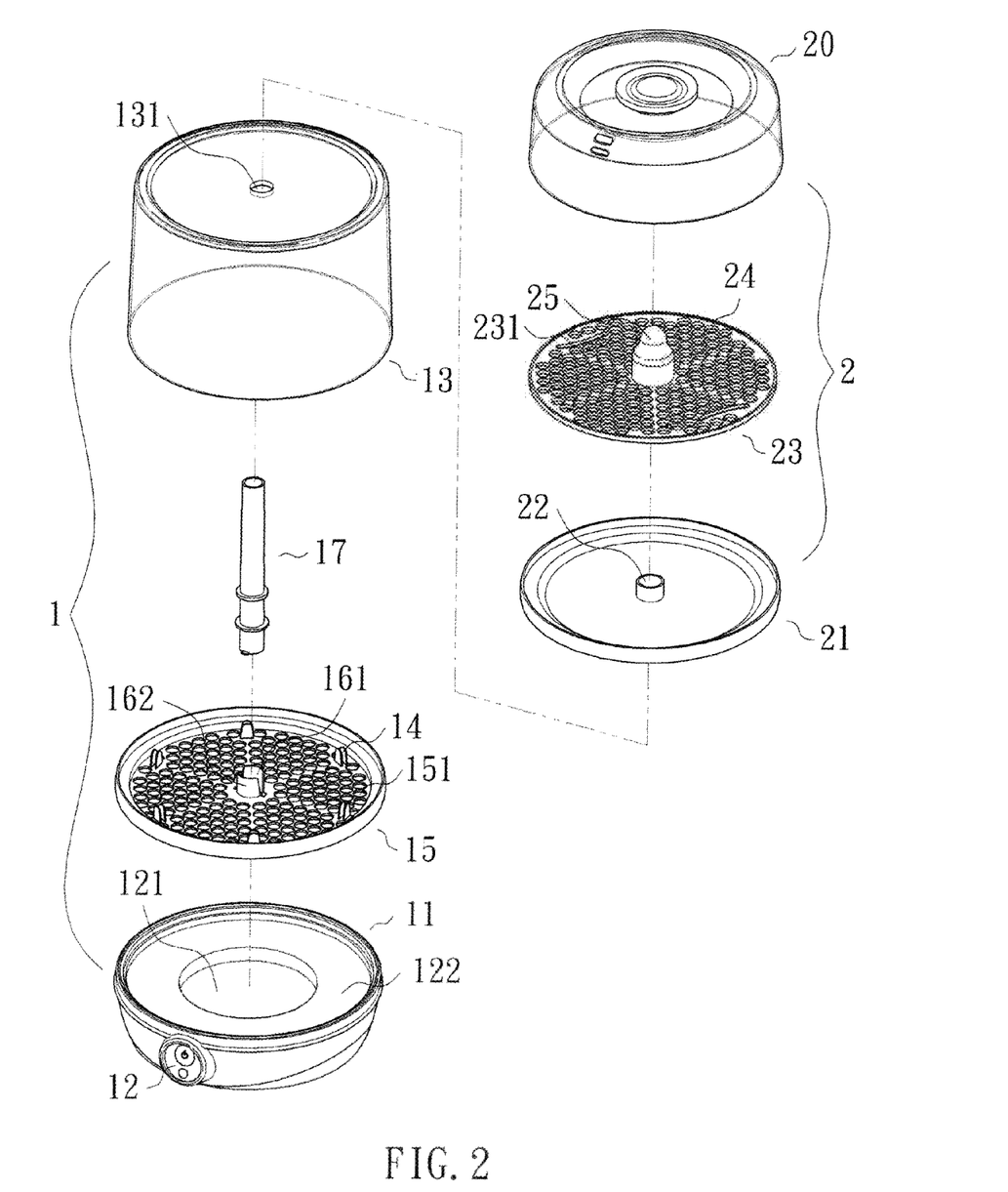
FIG. 2 is an exploded perspective view of the present invention.
Figure 3:
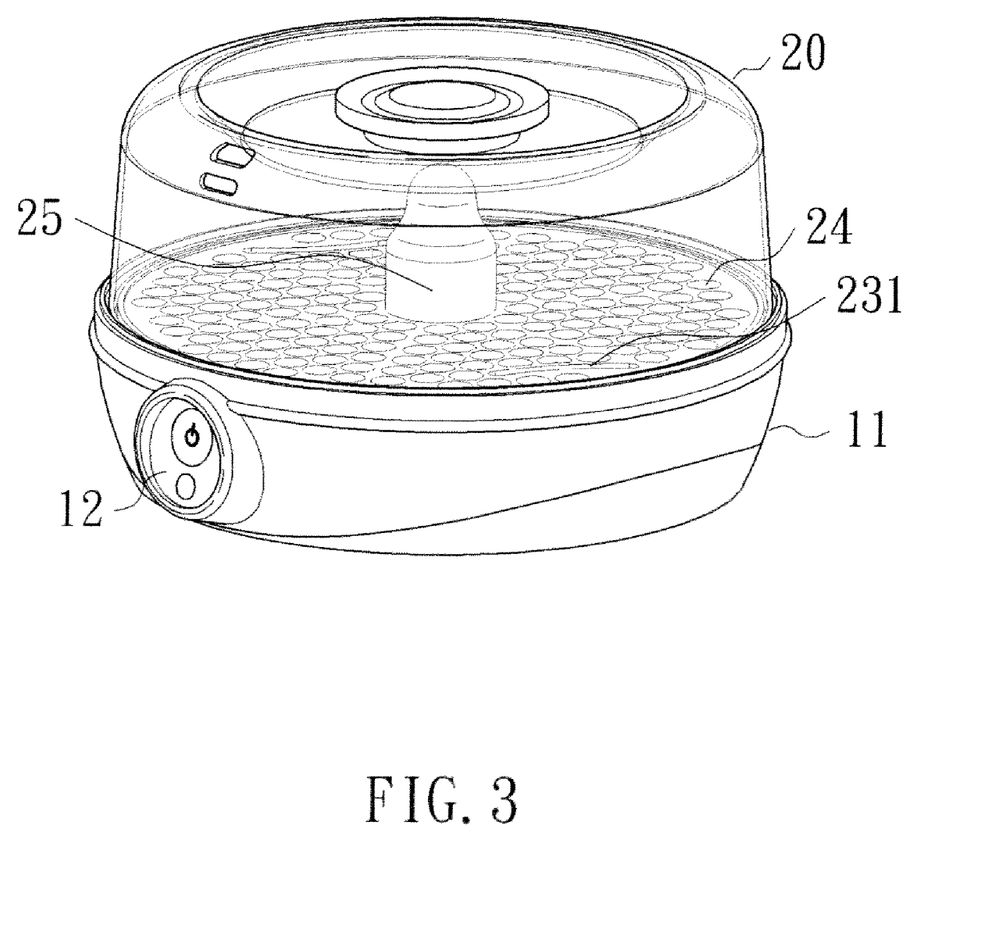
FIG. 3 is a perspective view of the present invention showing the secondary box of the secondary container and the third tray are disposed on the surface of the primary base.

Please refer to FIGS. 1, 2 and 3. If the height of the feeding bottle to be sterilized is smaller or the feeding bottle can be disposed horizontally, the secondary box 20 of the secondary container 2 and the third tray 23 can be disposed on the surface of the primary base 11 as shown in FIG. 3. Since the height of the secondary box 20 is slightly smaller than that of the primary box 13, such an arrangement can be used to sterilize the feeding bottle in a smaller space, thereby utilizing the heat more efficiently.

Figure 4:
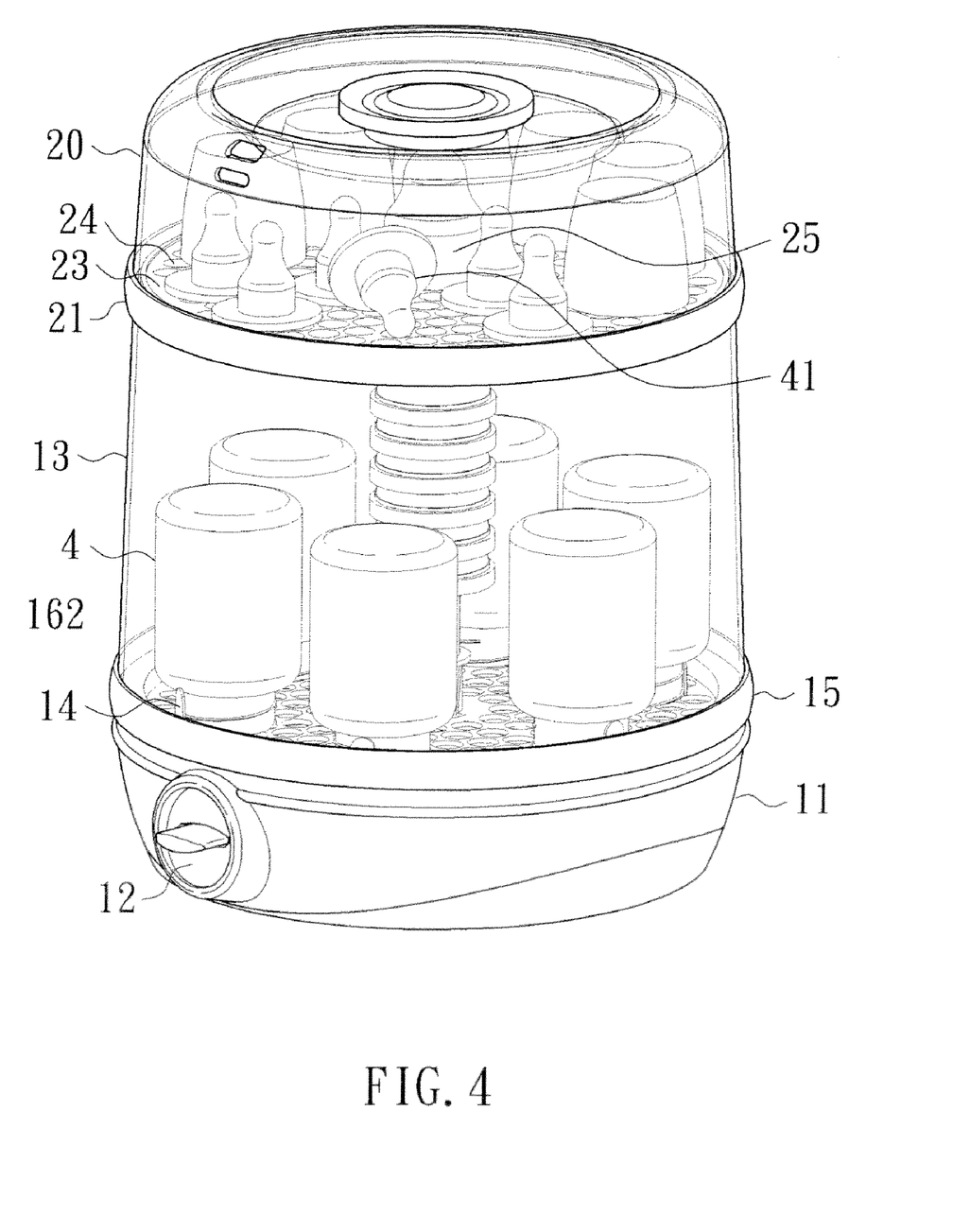
FIG. 4 is a perspective view of the present invention showing the secondary container is disposed on the top of the primary container.

Please refer to FIGS. 1, 2, and 4. The mouth of the feeding bottle 4 may be steadily inserted between the pair of secondary clip wings 14. As shown in FIG. 4, six feeding bottles may be disposed in the primary container 1 and the secondary container 1 is disposed on the top of the primary container 1. With this arrangement, the feeding bottles 4 disposed upright in the primary container 1 and bottle covers 41, feeding nipples or other smaller accessories disposed in the secondary container 2 can share the steam.

Figure 5:
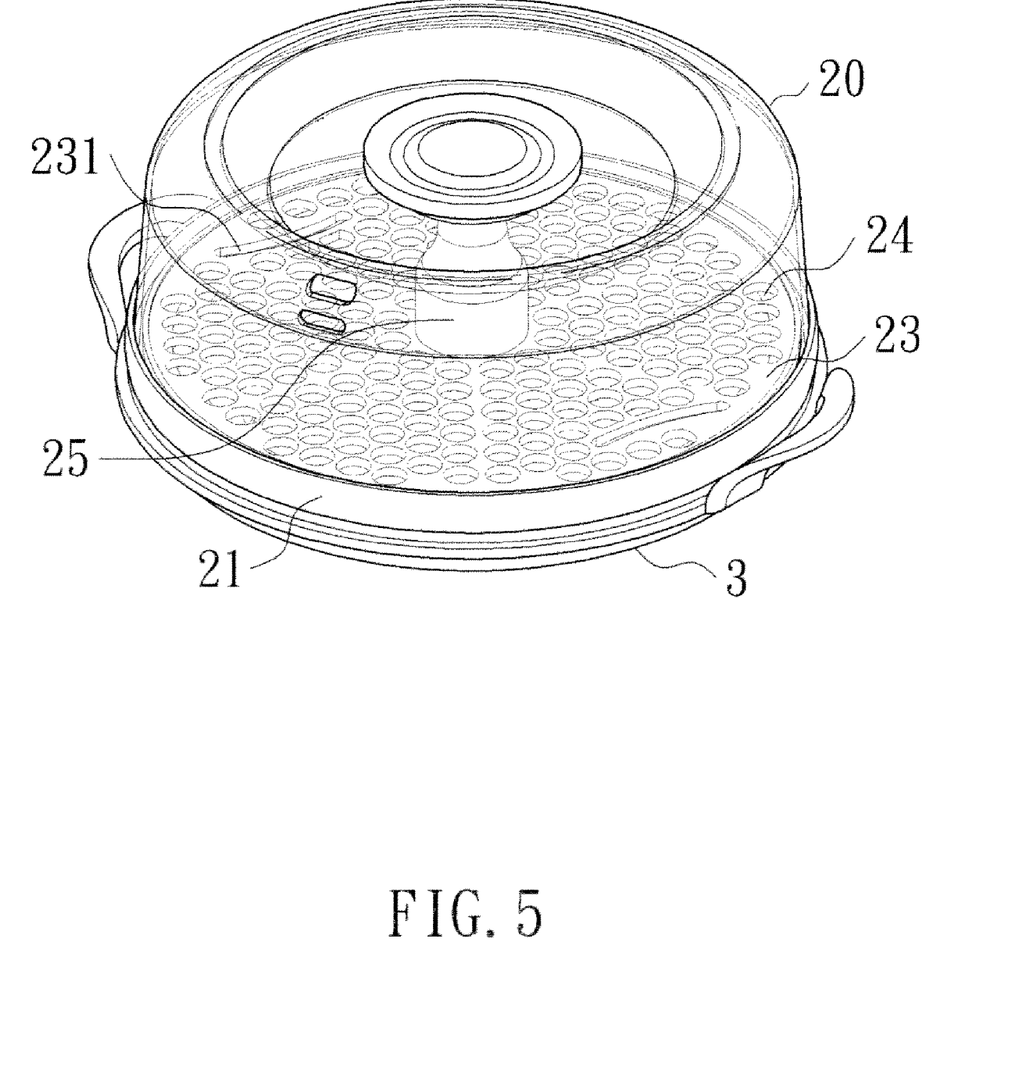
FIG. 5 is a perspective view showing the secondary box of the secondary container and the third tray are removed from the primary container and disposed in the microwave oven.

Please refer to FIGS. 1, 2 and 5. Alternatively, the secondary box 20 of the secondary container 2 and the third tray 23 may be disposed in the microwave oven. At this time, the user can use a fourth tray 3 to support the secondary box 20 and the third tray 23, thereby protecting the user from getting hurt due to their high temperature.

Figure 6:
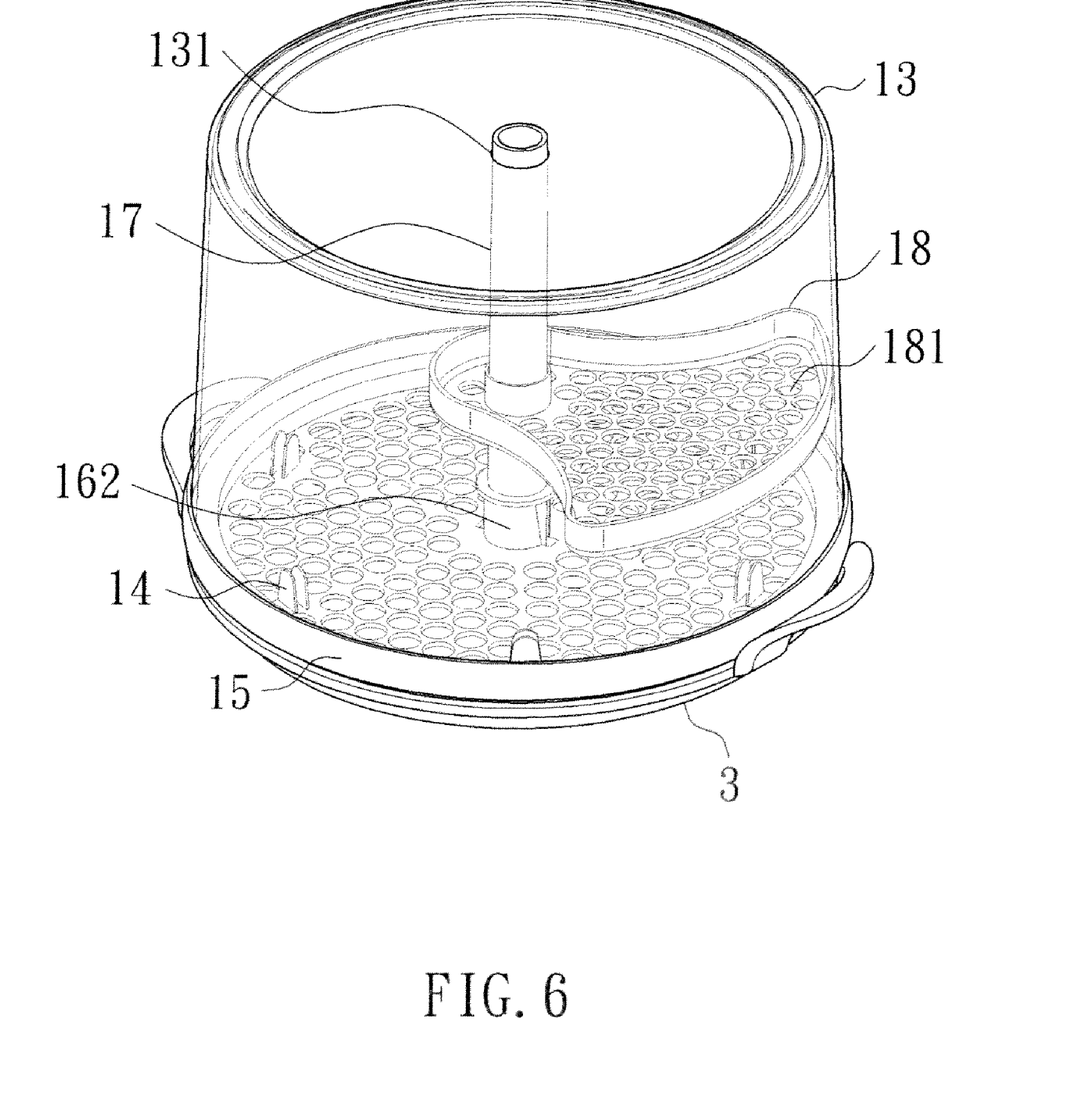
FIG. 6 is a perspective view showing the primary container of the present invention is used alone.

Please refer to FIGS. 1, 2 and 6. Alternatively, the secondary box 20 of the secondary container 2 and the third tray 23 may be removed from the primary container 1, and only the primary container 1 is used.

Figure 7:
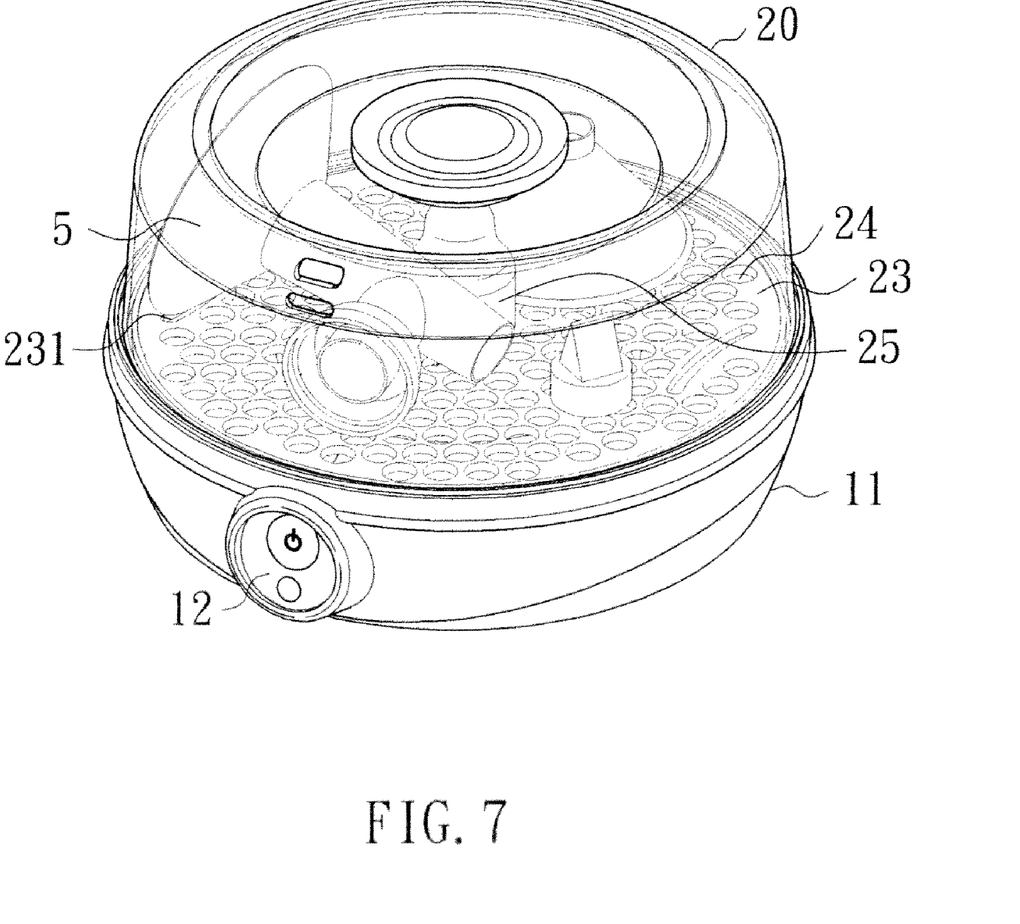

Please refer to FIG. 7. Alternatively, the secondary box 20 may be used to cover the primary base 11. A breast pump 5 is disposed between the secondary box 20 and the primary base 11 to be sterilized. The surface of the third tray 23 is provided with at least one insertion slot 231 (two shown in this figure) for allowing the breast pump 5 to be disposed therein.

Figure 8:
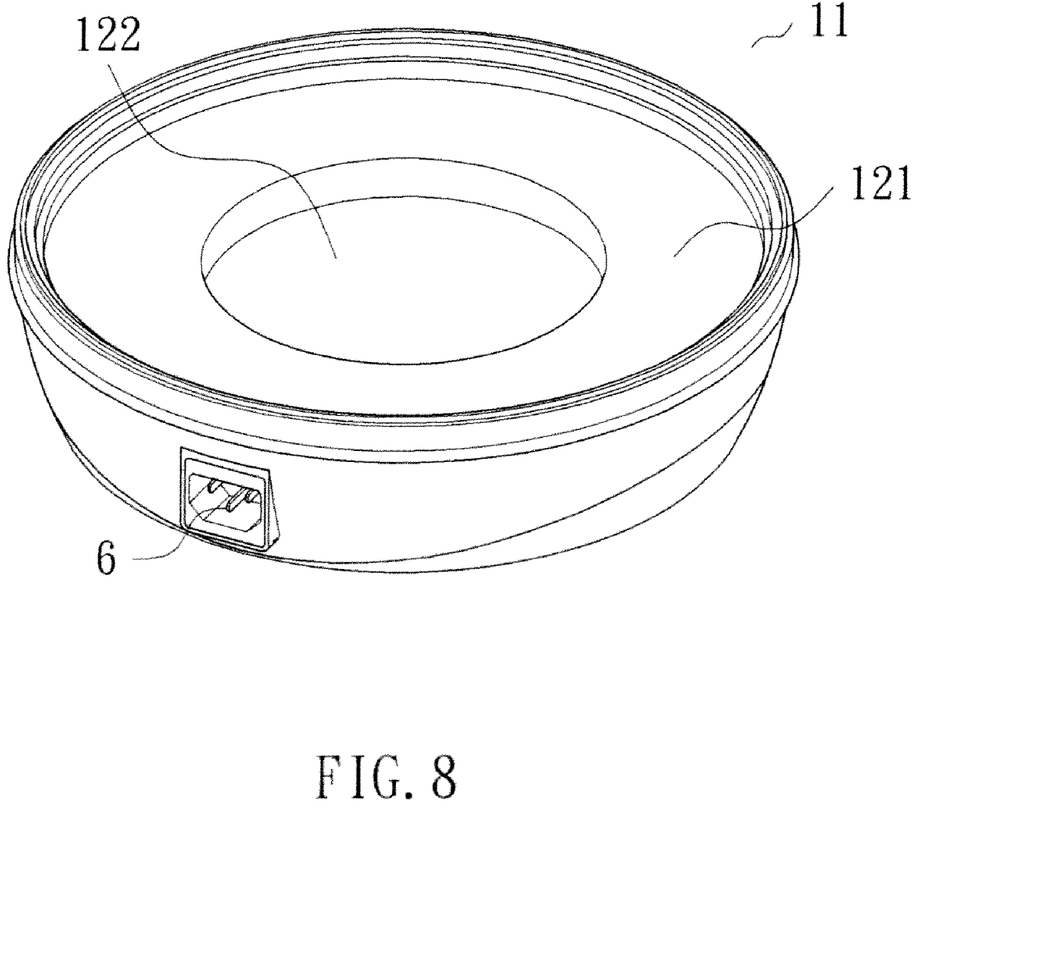
FIG. 8 is a perspective view showing that the present invention is provided with a socket.
Figure 9:
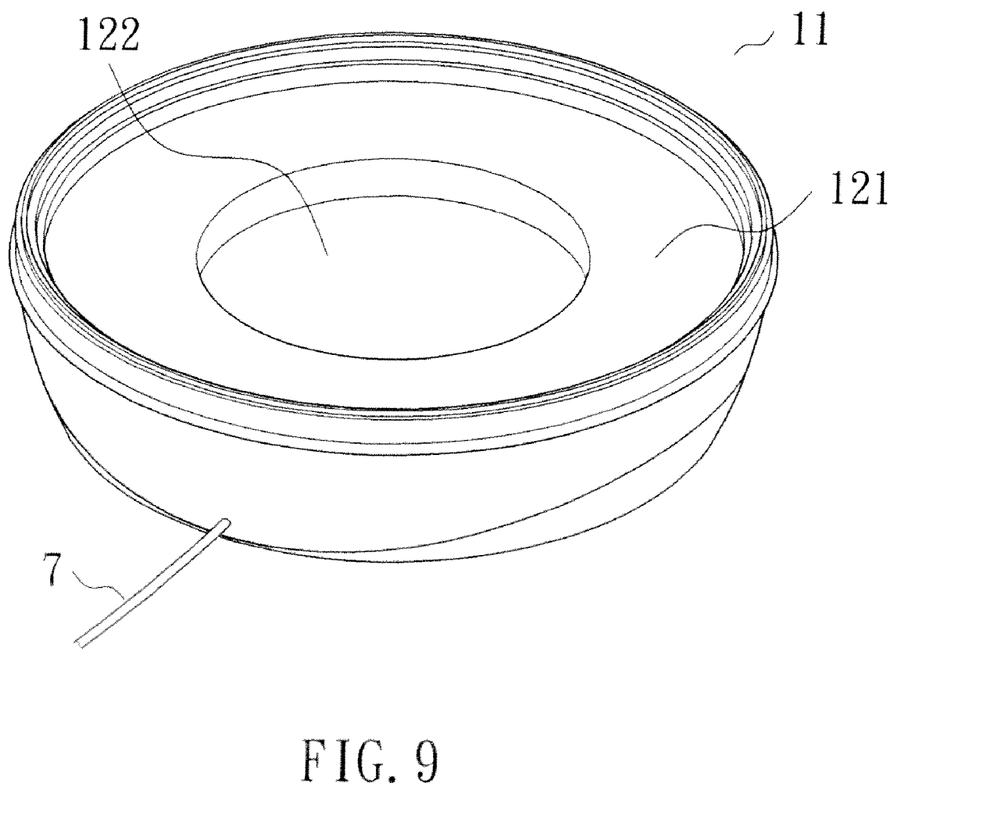
FIG. 9 is a perspective view showing that the present invention is provided with an electric cable.

Please refer to FIG. 8. The steam sterilizer of the present invention may be provided with a socket 6. With a connecting electric cable (not shown), the steam sterilizer can be electrically connected to a public outlet. Alternatively, as shown in FIG. 9, an electric cable 7 may extend from the steam sterilizer to be electrically connected to a public outlet.

According to the above, the present invention really has industrial applicability and it has not seen or used in public. Further, the present invention has non-obviousness, so that it conforms to the requirements for an invention patent.

The above disclosed embodiment is merely a preferred embodiment of the present invention. Various equivalent variations and modifications may be designed as known to those skilled in the art in view of the teachings of the present invention. Thus, all such variations and equivalent modifications are also embraced within the scope of the invention as defined in the appended claims.

What is claimed is:

1. A steam sterilizer, including:
   a primary container including a primary base, the interior of the primary base being provided with a heating means, the surface of the primary base being covered by a primary box having a downward opening, the primary base being provided with a water tray in communication with the primary box; and
   a secondary container movably provided on the top of the primary box, the secondary container including a secondary base, the surface of the secondary base being covered by a secondary box having a downward opening, the top of the primary box being provided with a primary through-hole for allowing steam to flow through, the bottom of the secondary base being provided with a secondary through-hole corresponding to the primary through-hole, the secondary container being movably disposed on the top of the primary container to share the steam.

2. The steam sterilizer according to claim 1, wherein the bottom of the secondary base is provided with a trough corresponding to the top of the primary box, the periphery of the trough is formed into a stepped portion for enclosing the outer edge of the top of the primary box, the stepped portion is configured to prevent the secondary container from falling off from the primary container.

3. The steam sterilizer according to claim 1, wherein the top surface of the primary base is provided with a first tray, the first tray is provided with a plurality of perforations.

4. The steam sterilizer according to claim 3, wherein the first tray is provided with two spaced primary clip wings, an insertion hole is formed between the two spaced primary clip wings, a pipe is inserted into the insertion hole, an upper section of the pipe is inserted into the primary through-hole and through the secondary through-hole, the pipe is disposed through a second tray.

5. The steam sterilizer according to claim 3, wherein the first tray is provided with two spaced secondary clip wings.

6. The steam sterilizer according to claim 1, wherein the top surface of the secondary base is provided with a third tray, the third tray is provided with a plurality of perforations.

7. The steam sterilizer according to claim 6, wherein the surface of the third tray is provided with a post.

8. The steam sterilizer according to claim 6, wherein the surface of the third tray is provided with in insertion slot.

* * * * *